(12) United States Patent
Yoon et al.

(10) Patent No.: US 8,778,988 B2
(45) Date of Patent: Jul. 15, 2014

(54) ENDOPEROXIDES AND METHODS OF PHOTOCATALYTICALLY SYNTHESIZING ENDOPEROXIDES

(75) Inventors: Tehshik P. Yoon, Madison, WI (US); Jonathan D. Parrish, Madison, WI (US); Michael A. Ischay, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 596 days.

(21) Appl. No.: 13/117,686

(22) Filed: May 27, 2011

(65) Prior Publication Data

US 2012/0302523 A1 Nov. 29, 2012

(51) Int. Cl.
*A61K 31/357* (2006.01)
*C07D 319/08* (2006.01)
*C07D 493/06* (2006.01)

(52) U.S. Cl.
USPC ........... 514/456; 549/356; 549/362; 549/364; 514/449; 514/451; 514/453

(58) Field of Classification Search
CPC ... A61K 31/357; C07D 319/08; C07D 493/06
USPC ........... 549/356, 362, 364; 514/449, 451, 456
See application file for complete search history.

(56) References Cited

U.S. PATENT DOCUMENTS

| | | | |
|---|---|---|---|
| 7,683,146 | B2 | 3/2010 | Gregorius et al. |
| 7,838,711 | B2 | 11/2010 | Herweck et al. |
| 7,915,414 | B2 | 3/2011 | Chi et al. |
| 7,923,557 | B2 | 4/2011 | Zhang et al. |

OTHER PUBLICATIONS

Fujita, et. al., Photooxygenation of 1,1-Diarylethylenes via Addition of Oxygen to the 1,4-Dimer Radical Cations, Catalyzed by 10-Methylacridinium Ion, Bull. Chem. Soc. Jpn., 1996, 743-749, vol. 69, Osaka University, Osaka, Japan.
Gollnick, et. al, Formation of 1,2-Dioxanes by Electron-Transfer Photooxygenation of 1,1-Disubstituted Ethylenes, Tetrahedron Letters, 1984, pp. 2735-2738, vol. 25, Pergamon Press Ltd., Great Britian.
Tamai, et. al., Photooxygenation of 1, w-Bis(diarylethenyl)alkanes via Photoinduced Electron Transfer: Formation of Bicyclic Peroxides, Tetrahedron Letters, 1993, pp. 2641-2644, vol. 34, Pergamon Press Ltd., Great Britain.

*Primary Examiner* — Golam M M Shameem
(74) *Attorney, Agent, or Firm* — Allison Johnson; Allison Johnson, P.A.

(57) ABSTRACT

A method of making an endoperoxide from a diene and oxygen in the presence of a photocatalyst having an excited state lifetime of at least 100 nanoseconds, the endoperoxide being represented by the formula:

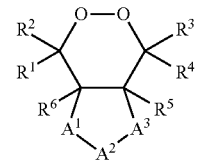

where
$R^1$ is an aryl substituted with at least one group selected from the group consisting of alkoxy, hydroxyl, halogen, carbamate, sulfonamide, silyloxy, amide, and combinations thereof or a substituted or unsubstituted heteroaryl, $R^2$ is hydrogen, alkyl, alkynyl, or aryl, $R^3$ is hydrogen, alkyl, alkynyl, or aryl, $R^4$ is alkynyl or aryl, $R^5$ is hydrogen or a substituent, $R^6$ is hydrogen or a substituent, and $A^1$, $A^2$, and $A^3$ are the same or different atoms and form a divalent group that combines with the two carbon atoms of the endoperoxide ring to form a saturated or unsaturated, substituted or unsubstituted ring system of a size of from five to six atoms.

31 Claims, No Drawings

ENDOPEROXIDES AND METHODS OF PHOTOCATALYTICALLY SYNTHESIZING ENDOPEROXIDES

BACKGROUND

The invention is directed to forming endoperoxides.

Ultraviolet light has been proposed and used to synthesize a number of molecules. Processes that use ultraviolet light often exhibit an uncontrolled reaction and produce low yields.

Endoperoxides have been formed using a variety of organic photosensitizers including dicyanoanthracene (DCA) and triphenylpyrylium tetrafluoroborate (TPP).

SUMMARY

In one aspect, the invention features an endoperoxide represented by the formula:

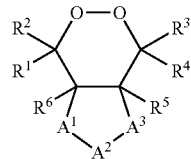

where $R^1$ is an aryl substituted with at least one group selected from the group consisting of alkoxy, hydroxyl, halogen, carbamate, sulfonamide, silyloxy, amide, and combinations thereof or a substituted or unsubstituted heteroaryl, $R^2$ is hydrogen, alkyl, alkynyl, or aryl, $R^3$ is hydrogen, alkyl, alkynyl, or aryl, $R^4$ is alkynyl or aryl, $R^5$ is hydrogen or a substituent, $R^6$ is hydrogen or a substituent, and $A^1$, $A^2$, and $A^3$ are the same or different atoms and form a divalent group that combines with the two carbon atoms of the endoperoxide ring to form a saturated or unsaturated, substituted or unsubstituted ring system having a size of from five to six atoms. In one embodiment, $R^1$ is 4-methoxyphenyl, 2-methoxyphenyl, 2,4-dimethoxyphenyl, 3,4-dimethoxyphenyl, or 3-halo-4-methoxyphenyl. In another embodiment, $R^4$ is phenyl, 2-trifluoromethyl-phenyl, 4-chloro-phenyl, or acetylene. In some embodiments, $R^1$ is 4-methoxyphenyl, 2-methoxyphenyl, 2,4-dimethoxyphenyl, 3,4-dimethoxyphenyl, or 3-halo-4-methoxyphenyl and $R^4$ is phenyl, 2-trifluoromethyl-phenyl, 4-chloro-phenyl, or acetylene.

In another embodiment, $R^1$ is an aromatic ring having a para position and an ortho position, and an electron donating substituent located at the para position of the aromatic ring, the ortho position of the aromatic ring, or a combination thereof.

In another aspect, the invention features a method of making an endoperoxide, the method including reacting a first compound and molecular oxygen in the presence of photocatalyst that has an excited state lifetime of at least 100 nanoseconds, the first compound including a diene represented by the formula

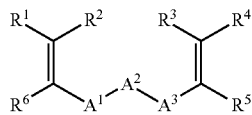

where $R^1$ is aryl substituted with at least one group selected from the group consisting of alkoxy, hydroxyl, halogen, carbamate, sulfonamide, silyloxy, amide, and combinations thereof, or a substituted or unsubstituted heteroaryl, $R^2$ is hydrogen, alkyl, alkynyl, or aryl, $R^3$ is hydrogen, alkyl, alkynyl, or aryl, $R^4$ is aryl or alkyne, $R^5$ is hydrogen or a substituent, $R^6$ is hydrogen or a substituent, and $A^1$, $A^2$, and $A^3$ are the same or different, substituted or unsubstituted atoms where $A^1$, $A^2$, and $A^3$ combine to form a saturated or unsaturated, substituted or unsubstituted chain of from three to four atoms. In some embodiments, $R^4$ further includes at least one substituent selected from the group consisting of alkoxy, halogen, and alkynyl. In other embodiments, $R^1$ includes an aryl group that includes at least one substituent selected from the group consisting of alkoxy and halogen. In some embodiments, $R^1$ includes an aryl group that includes at least two substituents selected from the group consisting of alkoxy and halogen.

In one embodiment, the photocatalyst exhibits an oxidation potential of greater than +0.9 volts. In other embodiments, the photocatalyst exhibits an oxidation potential of at least +1.3 volts. In some embodiments, the photocatalyst absorbs light having a wavelength of at least about 300 nanometers.

In another embodiment, $R^1$ is 4-methoxyphenyl, 2-methoxyphenyl, 2,4-dimethoxyphenyl, 3,4-dimethoxyphenyl, or 3-halo-4-methoxyphenyl. In other embodiments, $R^4$ is phenyl, 2-trifluoromethyl-phenyl, 4-chloro-phenyl, or acetylene. In one embodiment, $R^1$ is 4-methoxyphenyl, 2-methoxyphenyl, 2,4-dimethoxyphenyl, 3,4-dimethoxyphenyl, or 3-halo-4-methoxyphenyl and $R^4$ is phenyl, 2-trifluoromethyl-phenyl, 4-chloro-phenyl, or acetylene.

In other embodiments $R^1$ is an aryl group that includes a six carbon aromatic ring having a para position and an ortho position, and an electron donating substituent located at least one of the para position and the ortho position of the aromatic ring.

In another embodiment, the method further includes exposing the photocatalyst to radiation having a wavelength at least about 300 nanometers. In some embodiments, the photocatalyst includes a metal and the metal is selected from the group consisting of ruthenium, iron, osmium, cobalt, rhodium, iridium, nickel, palladium, platinum, manganese, technetium, rhenium, aluminum, silicon, gold, silver, mercury, titanium, zinc, copper, chromium, germanium, and combinations thereof. In other embodiments, the photocatalyst includes a metal and at least one ligand attached to the metal, the ligand including at least one of bipyrazyl, bipyridine, bipyrimidine, and cyanide. In other embodiments the photocatalyst includes at least one of tris(bipyrazyl)ruthenium (II), tris(bipyridyl)ruthenium (II), and bis(bipyrazyl) ruthenium (II) cyanate.

In one embodiment, the method produces a yield of at least 65% by weight endoperoxide based on the weight of the diene and oxygen. In another embodiment, the method produces a yield of at least 70% by weight endoperoxide based on the weight of the diene and oxygen.

In some embodiments, the photocatalyst has an excited state lifetime of at least 500 nanoseconds.

In another aspect, the invention features a method of making an endoperoxide, the method including reacting a diene and oxygen in the presence of a metal photocatalyst and radiation of a wavelength of at least 300 nm to form an endoperoxide. In some embodiments, the photocatalyst has an excited state life time of at least 100 nanoseconds. In other embodiments, the photocatalyst exhibits an oxidation potential of at least +1.3 volts. In another embodiment, the method produces a yield of at least 65% by weight endoperoxide based on the combined weight of the diene and the oxygen. In some embodiments, the yield includes at least 70% endoperoxide based on the combined weight of the diene and the oxygen. In one embodiment, the catalyst includes at least one of tris(bipyrazyl)ruthenium (II), tris(bipyridyl)ruthenium (II), and bis(bipyrazyl)ruthenium (II) cyanate. In another embodiment, the diene is represented by the formula

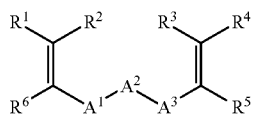

where $R^1$ is aryl substituted with at least one group selected from the group consisting of alkoxy, hydroxyl, halogen, carbamate, sulfonamide, silyloxy, amide, and combinations thereof, or a substituted or unsubstituted heteroaryl, $R^2$ is hydrogen, alkyl, alkynyl, or aryl, $R^3$ is hydrogen, alkyl, alkynyl, or aryl, $R^4$ is aryl or alkyne, $R^5$ is hydrogen or a substituent, $R^6$ is hydrogen or a substituent, and $A^1$, $A^2$, and $A^3$ are the same or different, substituted or unsubstituted atoms where $A^1$, $A^2$, and $A^3$ combine to form a saturated or unsaturated, substituted or unsubstituted chain of from three to four atoms.

In other aspects, the invention features a composition that includes an endoperoxide disclosed herein and a carrier.

The invention features a method of synthesizing endoperoxides using visible light. The method of synthesizing can produce good yields of the endoperoxide.

Other features and advantages will be apparent from the following description of the preferred embodiments and from the claims.

GLOSSARY

In reference to the invention, these terms have the meanings set forth below:

The term "substituent" means an atom or group other than hydrogen.

The term "alkyl" means a straight or branched saturated aliphatic hydrocarbon group that has at least 1 carbon atom.

The term "branched" means that at least one lower alkyl group (e.g., methyl, ethyl or propyl) is attached to a linear alkyl chain.

The term "alkoxy" means an alkyl group having an oxygen atom attached thereto.

The terms "aromatic ring" and "aryl" refer an unsaturated monocyclic or polycyclic-aromatic radical that includes carbon and hydrogen atoms.

The term "haloalkyl" means an alkyl group in which at least one atom is a halogen.

The term "alkenyl" means to an unsaturated aliphatic group analogous to an alkyl, but that contains at least one carbon-carbon double bond.

The term "alkynyl" means an unsaturated aliphatic group analogous to an alkyl, but that contains at least one carbon-carbon triple bond.

In complex structures, carbon chains may be branched, bridged, or cross-linked.

The term "heteroatom" means an atom that is not hydrogen or carbon.

The term "heteroalkyl group" means straight-chain and branched-chain structures analogous to alkyl groups in which at least one of the atoms in the chain is a heteroatom.

The term "heteroalkenyl group" means straight-chain and branched-chain structures analogous to alkenyl groups in which at least one of the atoms in the chain is a heteroatom.

The term "heteroalkynyl group" means straight-chain and branched-chain structures analogous to alkynyl groups in which at least one of the atoms in the chain is a heteroatom.

The term "C1-6 heteroalkyl" and "C1-C6 heteroalkyl" are used interchangeably to refer to a moiety that includes from 1 carbon atoms to 6 carbon atoms and at least one heteroatom.

The term "heterocyclic" means a closed ring structure analogous to carbocyclic groups in which at least one of the atoms in the ring is a heteroatom. Heterocyclic groups can be saturated or unsaturated closed ring structures. Heterocyclic groups can be attached to the core structure via a bond to either one of the heteroatoms in the ring of the heterocyclic group or one of the carbons in the ring of the heterocyclic group.

The term "heteroaryl" means a heterocyclic group that has aromatic character.

The groups discussed above may be "substituted or unsubstituted." The term "substituted" means that the group includes at least one substituent other than hydrogen.

The terms "substitution" or "substituted with" includes the implicit proviso that such substitution is in accordance with the permitted valence of the substituted atom and the substituent, and that the substitution results in a stable compound, e.g., which does not spontaneously undergo transformation such as by rearrangement, cyclization, or elimination.

When compounded chemical names, e.g., "alkylaryl" and "aryloxy," are used herein, they are understood to have a specific connectivity to the core of the chemical structure. The group listed farthest to the right (e.g., aryl in "alkylaryl"), is the group that is directly connected to the core. Thus, an "arylalkyl" group, for example, is an alkyl group substituted with an aryl group (e.g., phenylmethyl (i.e., benzyl)) and the alkyl group is attached to the core. An "alkylaryl" group is an aryl group substituted with an alkyl group (e.g., p-methylphenyl (i.e., p-tolyl)) and the aryl group is attached to the core.

DETAILED DESCRIPTION

The method of making an endoperoxide includes reacting a diene of formula I and molecular oxygen in the presence of a photocatalyst having an excited state lifetime of at least 100 nanoseconds to form an endoperoxide of formula II. The diene of formula I

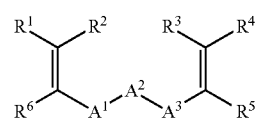

where
$R^1$ is aryl substituted with at least one group selected from the group consisting of alkoxy, hydroxyl, halogen, carbamate, sulfonamide, silyloxy, amide, and combinations thereof, or a substituted or unsubstituted heteroaryl,
$R^2$ is hydrogen, alkyl, alkynyl, or aryl,
$R^3$ is hydrogen, alkyl, alkynyl, or aryl, $R^4$ is aryl or alkyne,
$R^5$ is hydrogen or a substituent,
$R^6$ is hydrogen or a substituent, and
$A^1$, $A^2$, and $A^3$ are the same or different, substituted or unsubstituted atoms where $A^1$, $A^2$, and $A^3$ combine to form a saturated or unsaturated, substituted or unsubstituted chain of from three to four atoms.

The endoperoxide of formula II is

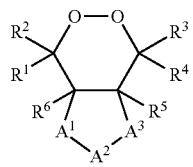

II where
$R^1$ is an aryl substituted with at least one group selected from the group consisting of alkoxy, hydroxyl, halogen, carbamate, sulfonamide, silyloxy, amide, and combinations thereof or a substituted or unsubstituted heteroaryl,
$R^2$ is hydrogen, alkyl, alkynyl, or aryl,
$R^3$ is hydrogen, alkyl, alkynyl, or aryl,
$R^4$ is alkynyl or aryl,
$R^5$ is hydrogen or a substituent,
$R^6$ is hydrogen or a substituent, and
$A^1$, $A^2$, and $A^3$ are the same or different atoms and form a divalent group that combines with the two carbon atoms of the endoperoxide ring to form a saturated or unsaturated, substituted or unsubstituted ring system of a size of from five to six atoms.

Useful alkyls include branched and straight-chain C1-C40 alkyl groups (i.e., an alkyl group that includes from one to 40 carbon atoms) including, e.g., methyl, ethyl, propyl, n-propyl, isopropyl, n-butyl, isobutyl, sec-butyl, tert-butyl, pentyl, hexyl, heptyl and octyl. The alkyl group optionally is substituted with at least one substituent.

Useful alkynyls include, e.g., straight chain and branched alkynyls including, e.g., acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl, and 9-decynyl. The alkynyl optionally is substituted with at least one substituent.

The aryl groups can be the same or different and include aromatic rings formed from at least four carbon atoms including, e.g., phenyl, naphthyl, biphenyl, indanyl, phenyl, tolyl, anthracenyl, fluorenyl, indenyl, azulenyl, naphthyl, and benzo-fused carbocyclic moieties including, e.g., 1,2,3,4-tetrahydronaphthyl and 5,6,7,8-tetrahydronaphthyl. The aromatic ring optionally is attached to other aromatic hydrocarbon rings or non-aromatic hydrocarbon rings.

The aryl groups of R2, R3 and R4 are each, independently of one another, unsubstituted or substituted with any substituent. Examples of suitable substituents for the R2, R3 and R4 aryl group include alkyl (e.g., C1-C6 alkyl), alkenyl (e.g., C2-C6 alkenyl), alkynyl (e.g., C2-C6 alkynyl), alkoxy (e.g., mono- and di-(C1-C6) alkoxy (e.g., methoxy, dimethoxy, and ethoxy)), halogen (e.g., chlorine, fluorine, bromine and iodine), hydroxyl, cyano, nitro, amino, alkylamino (e.g., mono- and di-(C1-C6)alkylamino), haloalkyl (e.g., C1-C6 haloalkyl), haloalkoxy (e.g., C1-C6 haloalkoxy), alkyl substituted amine (e.g., mono-, di- and tri-(C1-C6) alkyl substituted amine), alkyl substituted silyloxy (e.g., mono-, di- and tri-(C1-C6)alkyl substituted silyloxy), and combinations thereof. Examples of particularly useful substituted aryl groups include 4-methoxyphenyl, 2-methoxyphenyl, 2,4-dimethoxy phenyl, 3,4-dimethoxy phenyl, 3-bromo-4-dimethoxy phenyl, 4-t-butyl diisopropylsilyloxy phenyl, 4-t-butyl carbamoyl phenyl, 2-trifluoromethyl phenyl, 4-chloro phenyl, and acetyl phenyl.

The substituted R1 aryls include at least one electron donating substituent. The electron donating substituent is preferably located on the aryl group at the ortho position, the para position, or a combination thereof. Examples of suitable electron donating substituents include, e.g., alkoxy, hydroxy, halogen, silyloxy, carbamate, amide, sulfonamide, and combinations thereof. Useful alkoxy groups include branched and straight-chain alkoxy groups including, e.g., methoxy, ethoxy, isopropyloxy, propoxy, n-propoxy, butoxy, n-butoxy, and pentoxy. The alkoxy group optionally is substituted with at least one substituent.

Examples of useful silyloxy groups include t-butyl diisopropylsilyloxy, t-butyl-dimethyl-silyloxy-phenyl, and 2-(t-butyl-dimethyl-silyloxy)-3-fluoro-phenyl.

Carbamates are of the formula —NRC(O)—OR, where R is a group such as alkyl or aryl and is substituted or unsubstituted. Any alkyl group is suitable. Useful carbamates include mono- and di-(C1-C6) alkyl substituted amino carbamates including, e.g., methyl carbamate, t-butyl carbamate, benzyl carbamate, fluorenyl carbamate, and allyl carbamate.

Examples of useful amide groups include acetamido, benzamido, formamido, and phosphonamido.

The sulfonamides are of the formula —NRS(O)$_2$R, where R is a group such as alkyl or aryl and is substituted or unsubstituted.

Examples of useful R1 substituted aryl groups include 4-methoxyphenyl, 2-methoxyphenyl, 2,4-dimethoxy phenyl, 3,4-dimethoxy phenyl, 3-bromo-4-dimethoxy phenyl, 4-t-butyl diisopropylsilyloxy phenyl, 4-t-butyl carbamoyl phenyl, and acetoxy phenyl.

The R1 heteroaryls are aromatic rings that include at least one heteroatom, useful examples of which include, e.g., nitrogen, oxygen, silicon, sulfur, germanium, arsenic, selenium, tellurium, antimony, and phosphorous. Examples of useful heteroaryls include furyl, thienyl, pyrrolyl, pyrazolyl, oxazolyl, thiazolyl, imidazolyl, 1,2,3-triazolyl, 1,2,4-triazolyl, pyranyl, pyridyl, pyrimidinyl, 1,2,3-thiadiazolyl, 1,2,4-thiadiazolyl, 1,2,5-thiadiazolyl, 1,3,4-thiadiazolyl, indolyl, isoindolyl, benzofuryl, benzothienyl, benzimidazolyl, benzoxazolyl, purinyl, quinolinyl, isoquinolinyl, and thiazolidinyl.

The ring formed with the divalent group formed from A1, A2, and A3 can have a size of from five to seven atoms. Suitable atoms include, e.g., carbon, oxygen, nitrogen, silicon, sulfur, germanium, arsenic, selenium, tellurium, antimony, and phosphorous. Examples of useful divalent groups include e.g.,

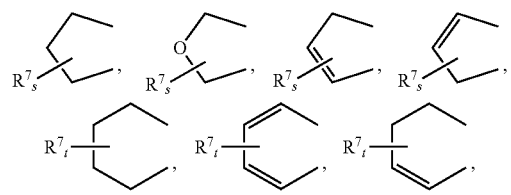

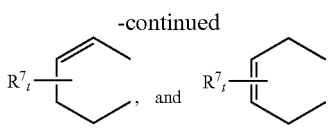

where the $R^7$'s are the same or different and are each hydrogen or a substituent, the indices s are the same or different and are a natural number from 0 to 8, and the indices t are the same or different and are a natural number from 0 to 10.

The substituents can be any suitable substituent including, e.g., alkyl, aryl, halogen, cyano, hydroxyl, nitro, alkoxy, aryloxy, alkylacyloxy, arylacyloxy, carboalkyl, carboaryl, carboalkoxy, carboaryloxy amino, amino, alkylamino, alkyl amino, dialkylamino, arylamino, diarylamino, alkylarylamino, acylamino, alkylcarbonylamino, arylcarbonylamino, carbamoyl, ureido, amidino, imino, isocyanato, nitro, carboxy, aminocarbonyl, alkylcarbonamido, arylcarbonamido), alkylthiocarbonyl, alkoxyl, phosphate, phosphonato, phosphinato, sulfates, sulfonato, sulfonamido, sulfamoyl, sulfo, sulfhydryl, alkylthio, arylthio, thiocarboxylate, alkylammonium, azido, heterocyclyl, alkylaryl, aromatic, heteroaromatic, and trifluoromethyl each either substituted or unsubstituted.

Specific examples of useful endoperoxides according to formula (II) include endoperoxides having the structure of formula II where i) R1 is 4-methoxyphenyl, R4 is phenyl, R2, R3, R5, and R6 are hydrogen, A1 and A3 are methyl and A2 is oxygen, ii) R1 is 2-methoxyphenyl, R4 is phenyl, R2, R3, R5, and R6 are hydrogen, A1 and A3 are methyl, and A2 is oxygen, iii) R1 is 2,4-dimethoxyphenyl, R4 is phenyl, R2, R3, R5, and R6 hydrogen, A1 and A3 are methyl and A2 is oxygen, iv) R1 is 3,4-dimethoxyphenyl, R4 is phenyl, R2, R3, R5, and R6 are hydrogen, A1 and A3 are methyl, and A is oxygen, v) R1 is 3-Bromine-4-methoxyphenyl, R4 is phenyl, R2, R3, R5, and R6 are hydrogen, A1 and A3 are methyl, and A2 is oxygen, vi) R1 is 4-t-butyldiisopropylsilyloxyphenyl, R2 is phenyl, R2, R3, R5, and R6 are hydrogen, A1 and A3 are methyl, and A2 is oxygen, vii) R1 is 4-t-butylcarbamoylphenyl, R4 is phenyl, R2, R3, R5, and R6 are hydrogen, A1 and A3 are methyl, and A2 is oxygen, viii) R1 is 4-methoxyphenyl, R4 is 4-methoxyphenyl, R2, R3, R5, and R6 are hydrogen, A1 and A3 are carbon, and A2 is oxygen, ix) R1 is 4-methoxyphenyl, R4 is 2-trifluoromethylphenyl, R2, R3, R5, and R6 are hydrogen, A1 and A3 are methyl, and A2 is oxygen, x) R1 is 4-methoxyphenyl, R4 is 4-chlorophenyl, R2, R3, R5, and R6 are hydrogen, A1 and A3 are methyl, and A2 is oxygen, xi) R1 is 4-methoxyphenyl, R2 is acetylphenyl, R2, R3, R5, and R6 are hydrogen, A1 and A3 are methyl, and A2 is oxygen, xii) R1 is 4-methoxyphenyl, R2 is hydrogen, R3 is methyl, R4 is phenyl, R5 and R6 are hydrogen, A1 and A3 are methyl, and A2 is oxygen, xiii) R1 is 4-methoxyphenyl, R2 and R3 are hydrogen, R4 is phenyl, R5 is methyl, R6 is hydrogen, A1 and A3 are methyl, and A2 is oxygen, xiv) R1 is 4-methoxyphenyl, R2, R3, R5, and R6 are hydrogen, R4 is 4-methoxyphenyl, A1 and A3 are methyl, and A2 is toluene sulfonamide, xv) R1 and R4 are 4-methoxyphenyl, R2, R3, R5, and R6 are hydrogen, A1 and A3 are carbon, and A2 is methyl diethylester, and xvi) R1 is 4-methoxyphenyl, R4 is 4-methoxyphenyl, R3, R5, and R6 are hydrogen, and A1, A2 and A3 are methyl.

Photocatalyst

The photocatalyst exhibits an excited state lifetime of at least 100 nanoseconds, at least 200 nanoseconds, or even at least 500 nanoseconds and absorbs light having a wavelength of at least about 300 nanometers (nm), at least about 325 nm, or even at least about 350 nm. The photocatalyst also has an oxidation potential of greater than +0.9 volt, at least +1.1 volt, at least +1.3 volt, as measured relative to a saturated calomel electrode.

Useful classes of photocatalysts include, e.g., metal photocatalysts and bulk semiconductor photocatalysts that are free of metal. Suitable metal photocatalysts include bulk semiconductor photocatalysts that include metal and photocatalysts that are in the form of a metal complex that includes a metal, at least one ligand, and a counter ion, which can be any ion. Useful metals include, e.g., transition metals (e.g., ruthenium, iron, osmium, cobalt, rhodium, iridium, nickel, palladium, and platinum), manganese, technetium, rhenium, aluminum, silicon, gold, silver, mercury, titanium, zinc, copper, chromium, germanium, and combinations thereof. Any suitable ligand can be used including, e.g., 2,2'-bipyridine, 2,2'-bipyrimidine, 2,2'-bipyraine, and combinations thereof. Useful commercially available metal photocatalysts include, e.g., tris(bipyrazyl)ruthenium (II), tris(bipyridyl)ruthenium (II), and bis(bipyrazyl)ruthenium (II) cyanide.

The catalyst is present in the reaction mixture in an amount of at least 0.1 mole %, at least 0.2 mole %, or even at least 0.4 mole %, no greater than 10 mole %, no greater than 5 mole %, or even no greater than 1 mole % based on the weight of the diene.

Process

Radiation is used to excite the photocatalyst and initiate the reaction between the diene and molecular oxygen. Preferably the photocatalyst is excited by radiation having a wavelength of at least about 300 nm, at least about 325 nm, or even at least about 350 nm. The radiation can be provided by a variety of useful light sources including, e.g., sunlight, incandescent lamp (e.g., molybdenum filament lamp and tungsten filament lamp), light emitting diode, fluorescent lamp, halogen lamp, black light, neon lamp, argon lamp, xenon lamp, hallow cathode lamp, plasma lamp, mercury vapor lamp, and combinations thereof.

The reaction preferably is carried out under an atmospheric pressure of at least one atmosphere and at a temperature of less than 25° C., less than 10° C., from about −10° C. to about 15° C., or even about 5° C., and in the presence of a molar excess of molecular oxygen based on the moles of diene starting material. In one useful process, the molecular oxygen is present in an amount of 4 atmospheres.

The diene is preferably dissolved in a solvent prior to exposure to the molecular oxygen and radiation. Useful solvents include, e.g., nitro-containing solvents (e.g., nitromethane, nitroethane, nitrobenzene, and 2-nitrotoluene), nitriles (e.g., acetonitrile, benzonitrile, and orthotolunitrile), and combinations thereof.

The process preferably results in a yield of at least 40%, at least 50%, at least 60%, at least 65%, or even at least 70% based on the total weight of the weight of the diene and oxygen starting materials.

Use

The endoperoxides are useful as synthetic intermediates and as active agents in pharmaceutical compositions.

Pharmaceutical Compositions

The endoperoxide can be formulated as a pharmaceutical composition. Typically, a pharmaceutical composition includes an endoperoxide and a physiologically acceptable carrier. For oral delivery, an endoperoxide can be incorporated into a formulation that includes pharmaceutically acceptable carriers such as binders (e.g., gelatin, cellulose, gum tragacanth), excipients (e.g., starch, lactose), lubricants (e.g., magnesium stearate, silicon dioxide), disintegrating agents (e.g., alginate, Primogel, and corn starch), sweetening or flavoring agents (e.g., glucose, sucrose, saccharin, methyl salicylate, aspartame, and peppermint), or combinations thereof. The formulation can be orally delivered in the form of enclosed gelatin capsules or compressed tablets. Capsules and tablets can be prepared by any conventional technique. Capsules and tablets also can be coated with various coatings known in the art to modify the flavors, tastes, colors, and shapes of the capsules and tablets. Liquid carriers such as oils can be included in capsules. Suitable oral formulations also can be in the form of suspension, syrup, chewing gum, wafer, elixir, and combinations thereof. If desired, conventional agents for modifying flavors, tastes, colors, and shapes of the special forms also can be included. For convenient administration by enteral feeding tube in patients unable to swallow, an endoperoxide can be dissolved in an acceptable lipophillic vegetable oil vehicle (e.g., olive oil, corn oil and safflower oil).

For parenteral delivery, an endoperoxide can be formulated as a solution or suspension, or in a lyophilized form capable of conversion into a solution or suspension form before use. In such formulations, diluents or pharmaceutically acceptable carriers such as sterile water and physiological saline buffer can be used. Other conventional solvents, pH buffers, stabilizers, anti-bacterial agents, surfactants, antioxidants, or combinations thereof also can be included. Useful diluents and pharmaceutically acceptable carriers include, e.g., sodium chloride, acetate, citrate or phosphate buffers, glycerin, dextrose, fixed oils, methyl parabens, polyethylene glycol, propylene glycol, sodium bisulfate, benzyl alcohol, ascorbic acid and combinations thereof. Parenteral formulations can be stored in any conventional containers including, e.g., vials and ampules.

For topical administration (e.g., nasal, bucal, mucosal, rectal, or vaginal applications), the endoperoxide can be formulated with a variety of carriers including, e.g., lotions, creams, ointments, gels, powders, pastes, sprays, suspensions, drops and aerosols, or encapsulated and then formulated with such carriers. Thickening agents, humectants, and stabilizing agents can be included in the formulation. Such agents include, e.g., polyethylene glycol, sorbitol, xanthan gum, petrolatum, beeswax, or mineral oil, lanolin, squalene, and combinations thereof. One form of topical administration includes delivery by a transdermal patch. Methods of preparing transdermal patches are disclosed, e.g., in Brown, et al., *Annual Review of Medicine,* 39:221-229 (1988), and incorporated herein.

The endoperoxide can also be delivered by sustained release using any suitable system including, e.g., implanting the endoperoxide in any suitable formulation into a subcutaneous space, e.g., beneath the anterior abdominal wall, of a mammal. A useful class of carriers for sustained release compounds includes hydrogels. Hydrogels are typically made by crosslinking high molecular weight biocompatible polymers into a network that swells in water to form a gel like material. Useful hydrogels include, biodegradable hydrogels, biosorbable hydrogels, hydrogels made of polyethylene glycols, collagen, or poly(glycolic-co-L-lactic acid) and combinations thereof. Useful hydrogels are also disclosed in Phillips et al., *J. Pharmaceut. Sci.* 73:1718-1720 (1984), and incorporated herein.

The invention will now be described by way of the following examples. All parts, ratios, percents and amounts stated in the examples are by weight unless otherwise specified.

EXAMPLES

Test Procedures

Test procedures used in the examples include the following. All ratios and percentages are by weight unless otherwise indicated.

Cytotoxicity Test Method

Human prostate cancer cells (Du145s) are treated for 72 hours with a test compound. The amount of cells living after 72 hours is quantified using CELLTITER-GLO luminescent cell viability assay (Promega Corporation, Madison, Wis.), which quantitates the amount of adenosine-5'-triphosphate present. The half maximal inhibitory concentration (IC50) is determined using curve fitting software, XLFIT 5.0 IDBS (ID Business Solutions LTD., Gilford Surrey, UK), to determine the concentration at which 50% cytotoxicity is observed.

Examples 1-19

Endoperoxides of Formula II

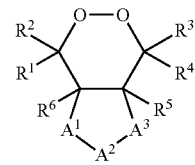

II were synthesized by reacting, at an ambient temperature of 5° C., a diene of formula I

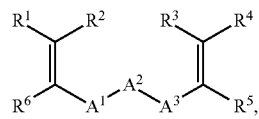

I which had been dissolved in nitromethane, and molecular oxygen under a pressure of 4 atmospheres in the presence of tris(bipyrazyl)ruthenium (II)bis(hexafluorophosphate) catalyst and radiation emitted by an illuminated 200 watt tungsten filament bulb. The reaction proceeded for the periods set forth under time in Table 1. The yield of endoperoxide produced by each synthesis and the ratio of the major diastereomer to other diastereomers is set forth in Table 1.

TABLE 1

| Sample | R1 | R4 | R2 | R3 | R5 | R6 | A1 | A2 | A3 | time | yield | d.r. |
|---|---|---|---|---|---|---|---|---|---|---|---|---|
| 1 | 4-MeOC$_6$H$_4$ (PMP) | Ph | H | H | H | H | CH$_2$ | O | CH$_2$ | 30 min | 92% | 6:1 |

TABLE 1-continued

| Sample | R1 | R4 | R2 | R3 | R5 | R6 | A1 | A2 | A3 | time | yield | d.r. |
|---|---|---|---|---|---|---|---|---|---|---|---|---|
| 2 | 3-MeOC$_6$H$_4$ | Ph | H | H | H | H | CH$_2$ | O | CH$_2$ | 24 h | 0% | — |
| 3 | 2-MeOC$_6$H$_4$ | Ph | H | H | H | H | CH$_2$ | O | CH$_2$ | 24 h | 45% | 10:1 |
| 4 | Ph | Ph | H | H | H | H | CH$_2$ | O | CH$_2$ | 24 h | 0% | — |
| 5 | 2,4-(MeO)$_2$C$_6$H$_3$ | Ph | H | H | H | H | CH$_2$ | O | CH$_2$ | 2 h | 58% | 4:1 |
| 6 | 3,4-(MeO)$_2$C$_6$H$_3$ | Ph | H | H | H | H | CH$_2$ | O | CH$_2$ | 1 h | 91% | 7:1 |
| 7 | 3-Br-4-MeOC$_6$H$_3$ | Ph | H | H | H | H | CH$_2$ | O | CH$_2$ | 12 h | 65% | 8:1 |
| 8 | 4-TIPSO—C$_6$H$_4$ | Ph | H | H | H | H | CH$_2$ | O | CH$_2$ | 2 h | 75% | 10:1 |
| 9 | 4-BocNH—C$_6$H$_4$ | Ph | H | H | H | H | CH$_2$ | O | CH$_2$ | 30 min | 96% | 6:1 |
| 10 | PMP | CH3 | H | H | H | H | CH$_2$ | O | CH$_2$ | 24 h | <5% | — |
| 11 | PMP | PMP | H | H | H | H | CH$_2$ | O | CH$_2$ | 30 min | 75% | >10:1 |
| 12 | PMP | 2-CF$_3$C$_6$H$_4$ | H | H | H | H | CH$_2$ | O | CH$_2$ | 2 h | 82% | 4:1 |
| 13 | PMP | 4-ClC$_6$H$_4$ | H | H | H | H | CH$_2$ | O | CH$_2$ | 2 h | 86% | 5:1 |
| 14 | PMP | —C≡C—Ph | H | H | H | H | CH$_2$ | O | CH$_2$ | 2 h | 82% | 2:1 |
| 15 | PMP | Ph | CH3 | H | CH3 | H | CH$_2$ | O | CH$_2$ | 2 h | 81% | >10:1 |
| 16 | PMP | Ph | H | CH3 | H | H | CH$_2$ | O | CH$_2$ | 6 h | 43% | 2:1 |
| 17 | PMP | PMP | H | H | H | H | CH$_2$ | NTs | CH$_2$ | 2 h | 73% | >10:1 |
| 18 | PMP | PMP | H | H | H | H | CH$_2$ | C(CO$_2$Et)$_2$ | CH$_2$ | 2 h | 92% | >10:1 |
| 19 | PMP | PMP | H | H | H | H | CH$_2$ | CH$_2$ | CH$_2$ | 2 h | 80% | >10:1 |

4-MeOC$_6$H$_4$ and PMP are 4-methoxyphenyl
Ph = phenyl
H = hydrogen
O = oxygen
h = hours
min = minutes
3-MeOC$_6$H$_4$ is 3-methoxyphenyl
2-MeOC$_6$H$_4$ is 2-methoxyphenyl
2,4-(MeO)$_2$C$_6$H$_3$ is 2,4-dimethoxyphenyl
3,4-(MeO)$_2$C$_6$H$_3$ is 3,4-dimethoxyphenyl,
3-Br-4-MeOC$_6$H$_3$ is 3-bromo-4-methoxyphenyl,
4-TIPSO—C$_6$H$_4$ is t-butyldiisopropylsilyloxy,
4-BocNH—C$_6$H$_4$ is t-butylcarbamate,
CH3 and CH2 are methyl,
2-CF$_3$C$_6$H$_4$ is 2-trifluorophenyl,
4-ClC$_6$H$_4$ is 4-chlorophenyl,
—C≡C—Ph is acetylphenyl,
NT is toluene sulfonamide, and
C(CO$_2$Et)$_2$ is (diethylmethylester)methyl The endoperoxides of Examples 1, 3, 5-7, 11-14, 16, 17, and 18 were tested according to the Cytotoxicity Test Method and determined to have anticancer effects on Du145s human prostate cancer cells.

Comparative 1

A reaction mixture that included 0.02 moles of a diene of formula I in which R1 and R2 are each 4-methoxyphenyl, and R2 and R3 are hydrogen and 0.5 mole % 9,10-dicyanoanthracene was exposed to radiation emitted by an illuminated 200 watt tungsten filament bulb in the presence of molecular oxygen at a pressure of 4 atmospheres. The system was allowed to react for thirty minutes at an ambient temperature of 5° C. The reaction produced less than 5% by weight endoperoxide and less than 5% by weight of a 2+2 cycloadduct of formula III

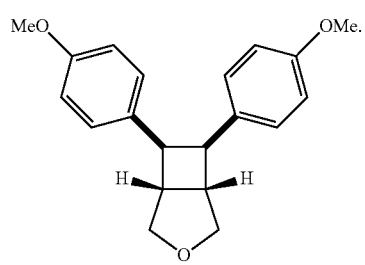

Comparative 2

A reaction mixture that included 0.02 moles of a diene of formula I in which R1 and R4 are 4-methoxyphenyl, and R2 and R3 are hydrogen, and 0.5 mole % triphenylpyrylium tetrafluoroborate was exposed to radiation emitted by an illuminated 200 watt tungsten filament bulb in the presence of molecular oxygen at a pressure of 4 atmospheres, and allowed to react for thirty minutes at an ambient temperature of 5° C. The reaction produced 20% by weight endoperoxide and less than 5% by weight of the 2+2 cycloadduct of formula III.

Comparative 3

A reaction mixture that included 0.02 moles of a diene of formula I in which R1 and R4 are 4-methoxyphenyl, R2 is hydrogen, and R3 is hydrogen, and 0.5 mole % tris(bipyridyl)ruthenium (II) bis(hexafluorophosphate), was exposed to radiation emitted by an illuminated 200 watt tungsten filament bulb in the presence of molecular oxygen at a pressure of 4 atmospheres, and allowed to react for thirty minutes at an ambient temperature of 5° C. The reaction produced less than 5% by weight endoperoxide and less than 5% by weight of a 2+2 cycloadduct.

Comparative 4

A reaction mixture that included 0.02 moles of a diene of formula I in which R1 and R4 are 4-methoxyphenyl, and R2 and R3 are hydrogen and 0.5 mole % tetraphenylporphyrin, was exposed to radiation emitted by an illuminated 200 watt tungsten filament bulb in the presence of molecular oxygen at a pressure of 4 atmospheres, and allowed to react for thirty minutes at an ambient temperature of 5° C. The reaction produced less than 5% by weight endoperoxide and less than 5% by weight of the 2+2 cycloadduct of formula III.

Other embodiments are within the claims.

All patents and other documents referred to herein are incorporated herein by reference.

What is claimed is:

1. An endoperoxide represented by the formula:

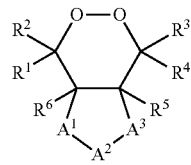

where
$R^1$ is an aryl substituted with at least one group selected from the group consisting of alkoxy, hydroxyl, halogen, carbamate, sulfonamide, silyloxy, amide, and combinations thereof or a substituted or unsubstituted heteroaryl,
$R^2$ is hydrogen, alkyl, alkynyl, or aryl,
$R^3$ is hydrogen, alkyl, alkynyl, or aryl,
$R^4$ is alkynyl or aryl,
$R^5$ is hydrogen or a substituent,
$R^6$ is hydrogen or a substituent, and
$A^1$, $A^2$, and $A^3$ are the same or different atoms and form a divalent group that combines with the two carbon atoms of the endoperoxide ring to form a saturated or unsaturated, substituted or unsubstituted ring system of a size of from five to six atoms.

2. The endoperoxide of claim 1, wherein $R^1$ is 4-methoxyphenyl, 2-methoxyphenyl, 2,4-dimethoxyphenyl, 3,4-dimethoxyphenyl, or 3-halo-4-methoxyphenyl.

3. The endoperoxide of claim 1, wherein $R^4$ is phenyl, 2-trifluoromethyl-phenyl, 4-chloro-phenyl, or acetylene.

4. The endoperoxide of claim 2, wherein $R^4$ is phenyl, 2-trifluoromethyl-phenyl, 4-chloro-phenyl, or acetylene.

5. The endoperoxide of claim 1, wherein $R^1$ is an aromatic ring having a para position and an ortho position, and an electron donating substituent at at least one of the para position and the ortho position of the aromatic ring.

6. A method of making the endoperoxide of claim 1, the method comprising:
reacting a first compound and molecular oxygen in the presence of a photocatalyst having an excited state lifetime of at least 100 nanoseconds to form an endoperoxide,
the first compound comprising a diene represented by the formula

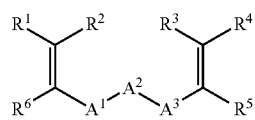

where
$R^1$ is aryl substituted with at least one group selected from the group consisting of alkoxy, hydroxyl, halogen, carbamate, sulfonamide, silyloxy, amide, and combinations thereof, or a substituted or unsubstituted heteroaryl,
$R^2$ is hydrogen, alkyl, alkynyl, or aryl,
$R^3$ is hydrogen, alkyl, alkynyl, or aryl,
$R^4$ is aryl or alkyne,
$R^5$ is hydrogen or a substituent,
$R^6$ is hydrogen or a substituent, and
$A^1$, $A^2$, and $A^3$ are the same or different, substituted or unsubstituted atoms where $A^1$, $A^2$, and $A^3$ combine to form a saturated or unsaturated, substituted or unsubstituted chain of from three to four atoms.

7. The method of claim 6, wherein $R^4$ further comprises at least one substituent selected from the group consisting of alkoxy, halogen, and alkynyl.

8. The method of claim 6, wherein $R^1$ comprises an aryl group comprising at least one substituent selected from the group consisting of alkoxy and halogen.

9. The method of claim 6, wherein $R^1$ comprises an aryl group comprising at least two substituents selected from the group consisting of alkoxy and halogen.

10. The method of claim 6, wherein the photocatalyst exhibits an oxidation potential of greater than +0.9 volts.

11. The method of claim 6, wherein the photocatalyst exhibits an oxidation potential of at least +1.3 volts.

12. The method of claim 6, wherein the photocatalyst absorbs light having a wavelength of at least about 300 nanometers.

13. The method of claim 6, wherein $R^1$ is 4-methoxyphenyl, 2-methoxyphenyl, 2,4-dimethoxyphenyl, 3,4-dimethoxyphenyl, or 3-halo-4-methoxyphenyl.

14. The method of claim 6, wherein $R^4$ is phenyl, 2-trifluoromethyl-phenyl, 4-chloro-phenyl, or acetylene.

15. The method of claim 12, wherein $R^4$ is phenyl, 2-trifluoromethyl-phenyl, 4-chloro-phenyl, or acetylene.

16. The method of claim 6, wherein $R^1$ is an aryl group comprising a six carbon aromatic ring having a para position and an ortho position, and an electron donating substituent located at least one of the para position and the ortho position of the aromatic ring.

17. The method of claim 6 further comprising exposing the photocatalyst to radiation having a wavelength at least about 300 nanometers.

18. The method of claim 6, wherein the photocatalyst comprises a metal selected from the group consisting of ruthenium, iron, osmium, cobalt, rhodium, iridium, nickel, palladium, platinum, manganese, technetium, rhenium, aluminum, silicon, gold, silver, mercury, titanium, zinc, copper, chromium, germanium, and combinations thereof.

19. The method of claim 6, wherein the photocatalyst comprises a metal and at least one ligand attached to the metal, the ligand comprising at least one of bipyrazyl, bipyridine, bipyrimidine, and cyanide.

20. The method of claim 6, wherein the photocatalyst comprises at least one of tris(bipyrazyl)ruthenium (II), tris(bipyridyl)ruthenium (II), and bis(bipyrazyl)ruthenium (II) cyanate.

21. The method of claim 6, wherein the method produces a yield of at least 65% by weight endoperoxide based on the weight of the diene and oxygen.

22. The method of claim 6, wherein the method produces a yield of at least 70% by weight endoperoxide based on the weight of the diene and oxygen.

23. The method of claim 6, wherein the photocatalyst has an excited state lifetime of at least 500 nanoseconds.

24. A method of making the endoperoxide of claim 1, the method comprising:
reacting a diene and molecular oxygen in the presence of a metal photocatalyst and radiation having a wavelength of at least 300 nm.

25. The method of claim 24, wherein the photocatalyst has an excited state life time of at least 100 nanoseconds.

26. The method of claim 24, wherein the photocatalyst exhibits an oxidation potential of at least +1.3 volts.

27. The method of claim 24, wherein the method produces a yield of at least 65% by weight endoperoxide based on the combined weight of the diene and the oxygen.

28. The method of claim 24, wherein the yield comprises at least 70% endoperoxide based on the combined weight of the diene and the oxygen.

29. The method of claim 24, wherein the catalyst comprises at least one of tris(bipyrazyl)ruthenium (II), tris(bipyridyl)ruthenium (II), and bis(bipyrazyl)ruthenium (II) cyanate.

30. The method of claim 24, wherein the diene is represented by the formula

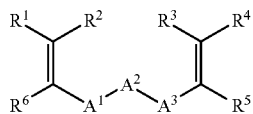

where $R^1$ is aryl substituted with at least one group selected from the group consisting of alkoxy, hydroxyl, halogen, carbamate, sulfonamide, silyloxy, amide, and combinations thereof, or a substituted or unsubstituted heteroaryl, $R^2$ is hydrogen, alkyl, alkynyl, or aryl, $R^3$ is hydrogen, alkyl, alkynyl, or aryl, $R^4$ is aryl or alkyne, $R^5$ is hydrogen or a substituent, $R^6$ is hydrogen or a substituent, and $A^1$, $A^2$, and $A^3$ are the same or different, substituted or unsubstituted atoms where $A^1$, $A^2$, and $A^3$ combine to form a saturated or unsaturated, substituted or unsubstituted chain of from three to four atoms.

31. A composition comprising:

the endoperoxide of claim 1; and a carrier.

* * * * *

UNITED STATES PATENT AND TRADEMARK OFFICE
CERTIFICATE OF CORRECTION

PATENT NO. : 8,778,988 B2  
APPLICATION NO. : 13/117686  
DATED : July 15, 2014  
INVENTOR(S) : Tehshik P. Yoon, Jonathon D. Parrish and Michael A. Ischay Page 1 of 1

It is certified that error appears in the above-identified patent and that said Letters Patent is hereby corrected as shown below:

IN THE SPECIFICATION:

Col. 2, Line 41, should read "position, and an electron donating substituent located at at least"

Signed and Sealed this  
Thirtieth Day of December, 2014

Michelle K. Lee  
*Deputy Director of the United States Patent and Trademark Office*